US00PP17873P3

(12) United States Plant Patent
Sproul

(10) Patent No.: US PP17,873 P3
(45) Date of Patent: Jul. 17, 2007

(54) MINIATURE ROSE PLANT NAMED 'SPROHEATHER'

(50) Latin Name: *Rosa hybrida*
Varietal Denomination: SPRoheather

(75) Inventor: James Sproul, Bakersfield, CA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 0 days.

(21) Appl. No.: 11/121,730

(22) Filed: May 5, 2005

(65) Prior Publication Data

US 2006/0253945 P1 Nov. 9, 2006

(51) Int. Cl.
*A01H 5/00* (2006.01)

(52) U.S. Cl. ..... Plt./128

(58) Field of Classification Search ..... Plt./121, Plt./128, 107
See application file for complete search history.

*Primary Examiner*—Howard J. Locker

(57) ABSTRACT

'SPRoheather' is a new and distinct variety of miniature rose plant, primarily identified by its fully double, classic hybrid tea form flowers of a medium pink, borne in clusters on a strong and upright plant. Flowers last a long time both on the plant and as cut flowers. Its dark green, semi-glossy foliage has shown exceptional resistance to powdery mildew.

1 Drawing Sheet

This present invention is being compared to 'Baby Claire', U.S. Plant application Ser. No. 10/119,400, abandoned, which is from this same breeding program, and with which it shares the same pollen parent. Both cultivars are pink, miniature rose plants, bearing their roses in clusters. 'Baby Claire' is a deeper pink with a greater fade upon aging than this present invention, with fewer clusters per plant and more of its flowers borne singly. Other similarities may be found in the texture of the petals and in the way the blooms open. Other differences may be seen in the plant habit. This present invention is an overall larger plant and more branched and with more vigor than 'Baby Claire'.

Genus and species: This present invention is a new variety of *Rosa hybrida* 'minima'.

Varietal denomination: This new cultivar has the varietal denomination of 'SPRoheather'.

BACKGROUND OF THE INVENTION

This new and distinct variety of miniature rose was created by James A. Sproul, under conditions of careful and controlled observation, at his nursery in Bakersfield, Calif. It is the result of a cross of a seedling of 'WEKjoe' (U.S. Plant Pat. No. 9,389), by 'JACient' (U.S. Plant Pat. No. 6,725), as the seed parent, by 'JACpoy' (U.S. Plant Pat. No. 9,015) as the pollen parent.

The primary objective of this breeding was to produce a new miniature rose variety with classic, hybrid tea formed flowers on a disease resistant bush. To meet this objective, the parents were chosen for their disease resistance as well as their exhibition form flowers. The objective was substantially achieved in this new, clear medium pink miniature rose having long tapered buds and good exhibition form.

This new cultivar, 'Sproheather', can be easily distinguished from its seed parent by size. The pink blend seed parent is a large-flowered hybrid tea seedling. 'SPRoheather' is a miniature rose.

'SPRoheather' is easily distinguished from its pollen parent by color. The Pollen parent, 'JACpoy', is a vibrantly colored orange and yellow blend miniature rose and 'SPRoheather' is a clear medium pink miniature rose, with yellow only at the base of the petals.

Other seedlings from this cross showed a wide variety of colors, with 'SPRoheather' being one of two miniature roses selected out for further evaluation. Four seedlings of the Mini-Flora class were also selected for further evaluation. Colors of these Mini-Floras are a pink blend, a russet, an orange blend and a yellow. The other mini selected for further evaluation is cream colored. These roses all have classic, exhibition hybrid tea form in fully double flowers.

BRIEF SUMMARY OF THE INVENTION

This present invention relates to a new and distinct cultivar of hardy, dwarf, bush type rose of the miniature class. This present invention may be compared to 'BENminn' (U.S. Plant Pat. No. 14,894). When grown outside in full sun, the flower color and form is very similar to that of 'BENminn'. The differences between 'BENminn' and 'SPRoheather' are in the plant habit. The plant habit on 'SPRoheather' is more compact and the entire plant is 6 inches or more shorter than 'BENminn'.

Among the characteristics which distinguish this new invention from others presently available, of which I am aware, are its unique combination of the following: the shade of medium pink of the flowers, borne primarily in clusters, that open slowly with superb, exhibition form on a well-branched and compact, miniature type bush with numerous prickles on the peduncles and many on the rachis, its dark green, semi-glossy foliage and its above average resistance to powdery mildew.

Other notable characteristics are its slight fragrance; its long, tapered, hybrid-tea form buds; its lasting quality as a cut flower and its near continuous blooming habit.

Subsequent to the origination of the cultivar, it was successfully asexually reproduced in Bakersfield, Calif. and Arroyo Grande, Calif., by budding on to Rosa Dr. Huey as well as by cuttings. The reproductions have run true in all respects.

BRIEF DESCRIPTION OF THE DRAWING

The accompanying color photographs show typical specimens of the vegetative growth and flowers of this new cultivar in different stages of development from four year old plants grown under plastic in Arroyo Grande, Calif.

BOTANICAL DESCRIPTION OF THE PLANT

The following observations of color values describe plants of this new invention, 'SPRoheather', at 3 or more years of age, grown in 6 inch azalea pots in a soiless mixture on a constant feed system, under plastic, in Arroyo Grande, Calif. Color References are made using The Royal Horticultural Society Colour Chart, except where common terms of color are employed.

Parents: ('WEKjoe' by 'JACient') by 'JACpoy'.
Botanical classification: *Rosa hybrida* 'minima'.
Commercial classification: Miniature.
Varietal denomination: 'SPRoheather'.

FLOWERS

This new cultivar bears its flowers in pyramidal clusters of 3 to 7 at the end of stems that originate from within large sprays. Sprays normally have 3 but may have as many as 5 lateral flowering stems plus a central or main flowering stem with not more than four of these stems within a spray terminating in clusters of flowers, and occasionally one or more of the stems terminating with a singly borne flower. The main stem of the spray terminates with the largest cluster and the lateral stems of the sprays usually terminate with smaller clusters of 3 or 4. The flowering stems constituting the spray are strong and straight, good for cutting.

Buds: Form is ovate with an acuminate tip and truncate base. Size is ¾-inch long and ½-inch in diameter at the widest point, just before the sepals divide.

Sepals: Extending ⅜-inch beyond the tip of the bud before they start to divide. As the flowers start to open, the sepals quickly reflex back to perpendicular with the stem and then back to the stem just as the petals begin to unfurl. They remain attached to the receptacle and fully reflexed back to the stem while the hip forms and ripens. There may be either 5 or 6 sepals on each flower.

The inside surfaces are pubescent, appearing near 147C. The outer surface has fine hairs and glands. The color is a medium green, near 144A, and the outer sepals have reddish anthocyanin coloration present.

The two outermost sepals have one or two, very small, peniculate, foliar appendages, 2/16- to 3/16-inch long and about 1/32-inch wide, along each margin and near evenly spaced stipitate glands. Length of the outer sepal varies from 15/16-inch to 1 2/16-inches long, with 1 1/16-inches being the most common length, and 10/32-inch to 12/32-inch wide, with 11/32 being the most common width.

The two or three innermost sepals have ciliate margins and no foliar appendages. When there is a third inner sepal present, it is always smaller than all the others, usually not more than 25/32-inch long and 9/32- or 10/32-inch wide. The other inner sepals vary from 26/32-inch to 31/32-inch long, with no two being the same length on each individual flower. The width of these inner sepals is usually 5/16-inch on the flowers in clusters and 6/16-inch on flowers borne singly on a stem within the spray.

The one sepal between the inner and outer sepals has one margin as those of the outer 2 sepals with the stipitate glands and a single foliar appendage, and one margin with stipitate glands along the upper half and is ciliate along the lower half and with no foliar appendages.

Receptacle: The color is near 144B and the surface appears glossy and glabrous. The diameter is 13/32-inch and the height is ⅜-inch. The profile is cupped shaped. The top is circular and 7/16-inch in diameter. The color of the upper surface is near 154D, a very light green-yellow.

Peduncle: The main or central peduncle of each cluster of flowers is straight and strong while the lateral peduncles are strong and curved slightly in the direction of the prevailing sun. Color is yellow green, near 144B, anthocyanin coloration absent. Peduncles are covered with numerous prickles, hairs and stipitate glands. The length is generally around 1¼-inches and the main or central peduncle of a cluster is often a little longer, up to 1½-inches in total length. Diameters of the peduncle average ⅛-inch and may be 1/64-inch greater or smaller. The main or central peduncle of each cluster always has the largest diameter in that cluster.

Near the base of each peduncle usually is a single or pair of nearly opposite peniculate, foliar appendages with truncate bases and acuminate apices, bearing some resemblance to the stipules. Occasionally there will be a small, single, bi-lobed or tri-lobed leaf attached to the foliage appendage. Occasionally a larger version of these foliar appendages can also be found with a short petiole and a predominate pair of stipules. The size, location and frequency of these foliar appendages appear random. All foliar appendages to the peduncle have the same coloring, margins and surface appearance as the new foliage. Most of these foliar appendages have a bud-eye located at the point of attachment to the peduncle.

Bloom: When fully expanded the bloom measures 2¾-inches across and ¾-inch deep. At perfect exhibition stage, the bloom measures 1½- to 2-inches across. From the time the sepals start to divide, the flower normally takes 3 to 4 days to open to exhibition stage and 6 to 9 days to reach full open stage with stamens showing. The flower remains full open for 3 to 6 days before the petals start to fade and lose their turgor. Faded petals hold on the receptacle for 5 to 7 days or more. The upper profile is high centered at first. Petals begin reflexing as they start to unfurl. The lower profile is cupped. When full open the upper and lower profiles are flattened convex. Cut flowers can last 10 to 14 days. Fragrance is slight.

Petals: The flowers have between 20 and 34 petals and 2 to 8 petaloids, with each flower within a cluster having a different count. The average petal count is 27 petals. The texture of the petals is velvety on both upper and lower surfaces. Both surfaces appear glabrous. The width of the outer petals is 1⅜-inches to 1¼-inches and the length is 1¼- to 1 5/16-inches. The form of the outer petals is broad obovate. The width decreases progressing towards the center of the flower, with the inner petals being simply obovate. Margins are entire. The apex is acute. Outer petals may have two apices or one single one that is off center or arcuate. The base of the outer petals is obtuse. The base of the intermediate petals is oblique. Inner petals are attached to the receptacle by a small stipe, which may actually be a modified filament.

Petaloids: Petaloids are often emarginate or cleft with a stipe or modified filament to attach to the receptacle. They vary in width from ½-inch down to 3/16-inch. Their coloring is the same as that of the inner petals, except for a streak of white, near 2D, from the base to the cleft in the outer margin. The streak can be seen on both the upper and lower surfaces of the petaloids.

Color of flowers: When the sepals first divide the color is near 50B, Rhodonite Red. During the first few days the color of the upper surface of the petals at the center of the flower is dawn pink, near 49A, with the basal area and point of attachment being a Naples yellow, near 11C. The reverse of the inner petals is Neyron rose, near 55C, and a Mimosa yellow, near 8C, at the base and point of attachment. The rest of the surface has the yellow suffused with the Neyron rose from the outer edge. Outer petals are a little lighter shade, between 55D and Venetian pink 49C, and a light yellow at the base and point of attachment, near 2C and near 2B, respectively. The reverse of the outer petals is rose Bengal, near 57D and the basal area and point of attachment are a very light yellow, both near 2D.

After 5 or more days, when the flower is full open, the colors have lightened very little. The upper surface of the inner petals becomes Neyron rose, between 55B and 55C and the base of the petals and point of attachment has become Mimosa yellow, near 8C and 8B, respectively. The reverse has become Spiraea Red, between 63B and 63C, where the petal edges roll under and the rest of the reverse being lighter pink, near 56B, and blending into the Mimosa yellow, near 8D, of the basil area. The point of attachment is a darker Mimosa yellow, near 8C. The upper surfaces of the outer petals have become Neyron rose, near 55C, and the basal area and point of attachment are a very light yellow, near 2D and 2C, respectively. The reverse is a darker Neyron rose, near 55B, where the petal edge rolls under and becoming near 55D by mid petal, with the basal area coming up to mid petal and the point of attachment both being near 2D, a very light yellow.

As the bloom ages it lightens overall, first to near 62C, with the outer petals near 62D and finally, before petals drop, to 62D and the outer petals, to near 65D. The general tonality of the plant is medium pink.

REPRODUCTIVE ORGANS

Stamens, filaments and anthers are attached in small clusters and very tight together, along the upper perimeter of the receptacle, adjacent to the petals. The count ranges from 290 to 320. The corresponding amount of pollen is very little compared to the number of stamens but there is still an ample amount from each flower. The length of the filaments closest to the petals is up to 5/16 inch. The filaments closest to the center of the flower are nearly doubled over, recurving in towards the center of the flower. When straightened out, they measure ¼-inch in length. Filaments in-between the innermost and outer-most stamens are varying lengths between 5/16-inch and ¼-inch. Their color is a very light yellow, near 2D. Before the blossom opens, the anthers and pollen are the same color, near 2D. When the flower opens the pollen along the edges of the anthers becomes of a deep Indian yellow, near 17A. Pollen is virile.

Pistils, styles and stigmas are surrounded by hairs in an alveola located at the center of the upper surface of the receptacle. The quantity of pistils is about one-fourth as many as the stamens. Styles are very thin and straight, ranging from 9/32- to 10/32-inch long. The upper half of the styles is near 60C, a deep purple-pink. The lower half is a greenish white, near 157C. The stigmas are near 159A, of the orange white group.

'SPRoheather' does set hips that become oblate as they mature. They are rather large for a mini. Seeds may protrude slightly from the top of the hip. The diameter of the height and width are nearly equal. When mature, the hip is still mostly green, with only a small portion taking on a greyed-orange tone.

PLANT

The plant habit of 'SPRoheather' is upright and well branched, growing 18 to 24 inches tall and up to 24 to 30 inches wide. The main stems of the plant have from 7 to 8 mature leaves. The distance between nodes is around ¾-inch near the base of the stems and variable, from ¾-inch to around 1½-inches, in no pattern, for the remainder of the stem. Flowering stems are most often near 4½-inches long, are generated from within a spray of flowering stems, and usually terminating with a cluster of 3 to 7 flowers, but may also have a single flower.

Foliage: Leaves have 3 to 7 leaflets, with the 3 leaflet leaves being primarily on the stems of the sprays. Length of mature leaves ranges from 3¾-inches to 4¼-inches from attachment to the stem to the tip of the terminal leaflet, when measured along the rachis. The terminal leaflet measures from 1½-inches to 2⅛-inches long with 1¾-inches being the most common length. The width varies from 1 inch to 1 3/16-inches, and 1 1/16-inch is the most common width.

The shape of the leaflets is ovate with an acute tip. The base of the terminal leaflet is rounded. The base of the paired leaflets is obtuse. The upper surface is semi-glossy and the reverse is matte. The central vein and primary lateral veins protrude somewhat on the underside of the leaflets. The primary lateral views are not evenly spaced, nor do they consistently run parallel, with some lateral veins branching into two, near equal, laterals. When this branching occurs it is most often one-third of the distance from the outer margin. There seems to be no consistency in which lateral veins form into these branches.

Leaf margins are serrate, sometimes singly and near even and sometimes double but usually mixed single and double on each leaf, with no consistency. The upper surface of the foliage appears semi-glossy and glabrous. The under surface is leathery.

The color of the upper surface of the new foliage is dark green, near 147A. The veins, especially the central vein, and the margin appear near 185B, *chrysanthemum* crimson. The under surface is lighter, near 147B and may be lightly flushed with anthocyanin coloring, near 185B. The older foliage is also near 147A. Anthocyanin coloring is absent except at the juncture of the rachis and petiolules. The under surface is near 147B and the primary vein appears a lighter yellow-green, near 146D.

Petioles: On a 5 leaflet leaf the length of the petiole varies from ¾-inch to 1 1/16-inches. On a 7 leaflet leaf it measures 7/16-inch to ¾-inch. Both have a diameter of 3/32-inch. Color on young foliage, noticeable in the groove of the upper side, is a medium yellow-green, near 146C, and the ridges are flushed with a purple-red, near 184B. The underside is near 144A, lettuce green. The color along the ridges on the upper side of the petiole of the old foliage is the same as that of the upper side of its leaflets, near 147A, and lighter, near 147B, in the groove. The underside is lighter still, near 146D.

Rachis: The rachis, measured from the point of attachment of the basal leaflets to the point of attachment of the terminal leaflet, varies from 1¼-inches to 1⅜-inches on the 7 leaflet leaves and from 25/32- to 1-inch on five leaflet leaves. Color is the same as that of the petioles. There are 7 or 8 prickles along the underside of the rachis. 3 to 7 of the prickles will be ⅛-inch long and the remainder will be between 1/16- and 1/32-inch long.

Petiolules: On the upper side of young leaves the color appears near 187D, a red-purple. The underside is near 144A, lettuce green. The color of the upper side of the petiolules on older foliage is the same as the color of the upper side of the petioles and rachis, dark green, near 147A along the ridges, and lighter, near 147B, in the groove. The underside is lighter, near 146D. The length on the first pair down from the terminal leaflet is 3/32-inch. The length of the petiolules on the second and third pair of leaflets is 2/32-inch. The texture of the upper side appears glabrous. The underside has prickles and hairs.

Stipules: There are stipules attached to each side of the petioles, beginning at the base of each leaf, where it attaches to the stem. On a mature leaf they measure from 16/32- to 18/32-inch in length attached to the petiole and an additional ⅛-inch angled outward at about a 45 degree angle. Pairs are very nearly even. The color is generally a dark yellow green on mature leaves, near 146A on the adaxial surface and near 146B on the reverse. Margins are finely serrated with the very edge rolling under.

Wood: Main stalks are 10/32- to 11/32-inch in diameter. Laterals are 7/32- to 8/32-inch in diameter. New and old wood appear glabrous. The color of the new wood is lighter yellow-green, near 144B. Old wood is a darker green, near 147B. Cuttings from soft, new growth produce roots in 10 to 14 days under controlled, greenhouse conditions.

Prickles: On the main stalks there are 0 to 3 prickles on any one inch of stem length but equaling 6 prickles on 3 inches of stem length. On the laterals, there are 1 to 6 prickles on one inch of stem but equaling 11 prickles on 3 inches of stem. On the laterals, there is one prickle on each side of the base of each petiole. The base of each prickle is obovate, ¼-inch long and ⅛-inch wide with the prickle length being ¼-inch, or the base is 3/16-inch long and 3/32-inch wide and the extension is 3/16-inch long. The upper profile is straight and may be angled down. The lower profile starts lunate from the base with an acuminate tip. The color of the young prickles is near 181C from the greyed-red group. When old, the base is near 160A from the greyed-yellow group and the extension is near 165C from the greyed-orange group. The prickles on the underside of the rachis are near 157D, from the green-white group, and the upper or straight side may be flushed near 185C from the greyed-purple group.

Disease resistance: 'SPRoheather' has demonstrated great resistance to powdery mildew. It is susceptible to black-spot and downy mildew. It has average resistance to rust.

Hardiness: 'SPRoheather' has proven hardy through testing in cold zones 8 and 9 and heat zones 4, 7 and 8, and is currently being tested in cold zone 5.

It is claimed:

1. A new and distinct cultivar of hardy, miniature rose plant is claimed, substantially as illustrated and described, characterized by buds and flowers of a medium pink, that open slowly, having long, tapered, hybrid-tea form buds, sepals reflexing well ahead of the opening bloom, and with the flowers being borne primarily in clusters on an upright and well-branched plant with dark green, semi-glossy foliage and easy to reproduce by budding or soft wood cuttings.

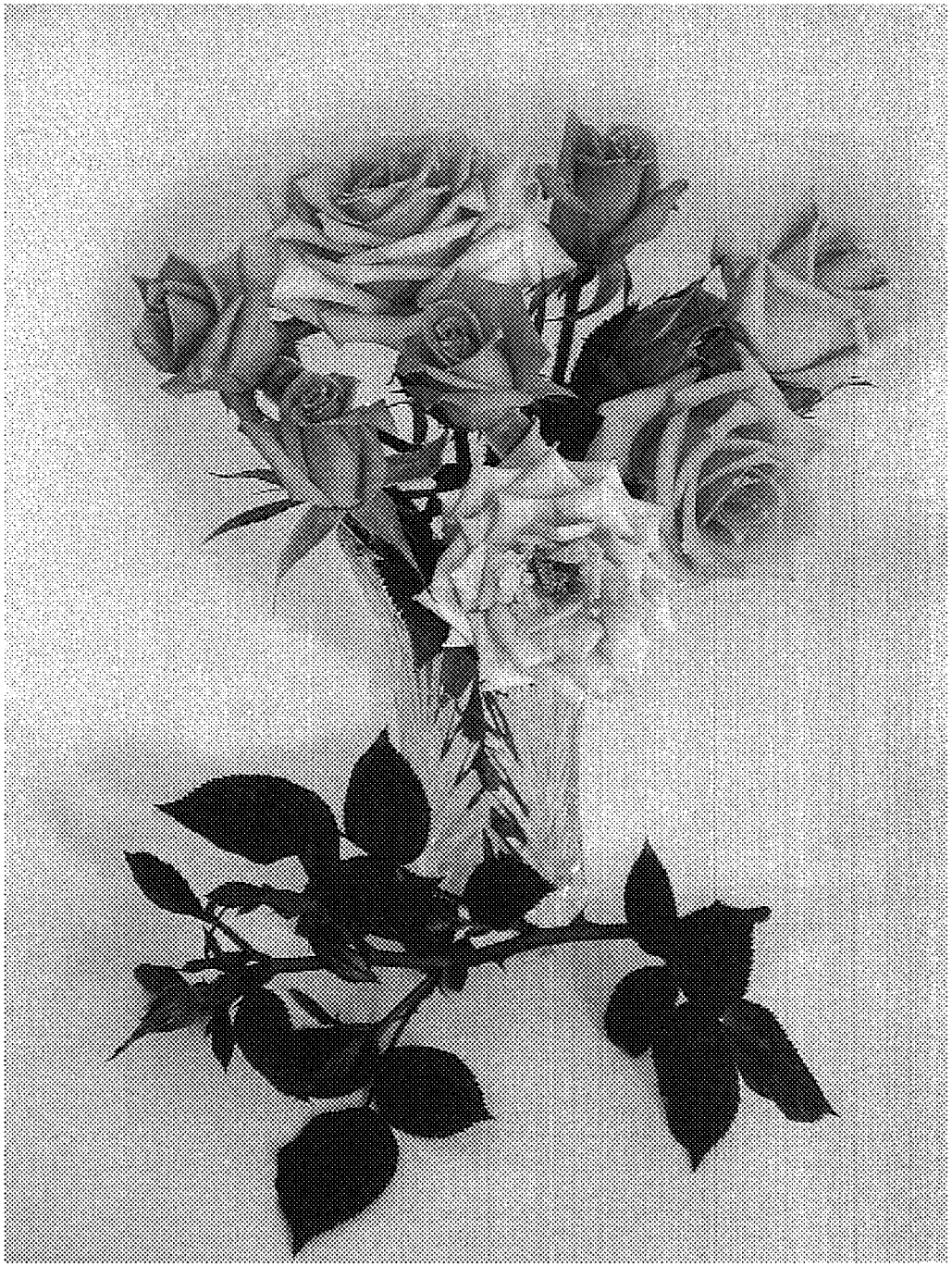

* * * * *